United States Patent [19]

Daugherty et al.

[11] Patent Number: 5,880,307
[45] Date of Patent: Mar. 9, 1999

[54] PROCESS FOR THE PREPARATION OF ALKYLHALOSILANES

[75] Inventors: Richard Dewayne Daugherty, Vevay, Ind.; Steven Kerry Freeburne, Edgewood; Paul Jacques Marion, Florence, both of Ky.; Oliver K. Wilding, Jr., Sully, South Glamorgan, United Kingdom

[73] Assignee: Dow Corning Corporation, Midland, Mich.

[21] Appl. No.: 24,378

[22] Filed: Feb. 17, 1998

[51] Int. Cl.$^6$ ...................................................... C07F 7/16
[52] U.S. Cl. ............................................................ 556/472
[58] Field of Search ............................................... 556/472

[56] References Cited

U.S. PATENT DOCUMENTS

| | | | |
|---|---|---|---|
| 2,380,995 | 8/1945 | Rochow et al. | 260/607 |
| 2,380,996 | 8/1945 | Rochow et al. | 260/607 |
| 5,015,751 | 5/1991 | Feldner et al. | 556/472 |
| 5,312,948 | 5/1994 | Freeburne et al. | 556/472 |
| 5,334,738 | 8/1994 | Pachaly et al. | 556/472 |
| 5,380,903 | 1/1995 | Degen et al. | 556/472 |
| 5,605,583 | 2/1997 | Margaria | 148/405 |
| 5,654,460 | 8/1997 | Rong | 556/472 |
| 5,712,405 | 1/1998 | Nakayama et al. | 556/472 |
| 5,777,146 | 7/1998 | Staussberger et al. | 556/472 |

*Primary Examiner*—Paul F. Shaver
*Attorney, Agent, or Firm*—Melvin D. Fletcher

[57] ABSTRACT

A process for the use of water granulated silicon in the preparation of alkylhalosilanes. The process comprises contacting an alkyl halide described by formula RX, with a particulate water granulated silicon containing greater than 0.5 to about 5.0 weight percent iron, in the presence of a catalyst composition comprising copper, at a temperature within a range of about 250° C. to 350° C. where R is selected from the group consisting of alkyls comprising one to about four carbon atoms and X is a halogen.

13 Claims, No Drawings

PROCESS FOR THE PREPARATION OF ALKYLHALOSILANES

BACKGROUND OF INVENTION

The invention is a process for the use of water granulated silicon in the preparation of alkylhalosilanes. The process comprises contacting an alkyl halide described by formula RX, with a particulate water granulated silicon containing greater than 0.5 to about 5.0 weight percent iron, in the presence of a catalyst composition comprising copper, at a temperature within a range of about 250° C. to 350° C., where R is selected from the group consisting of alkyls comprising one to about four carbon atoms and X is a halogen.

The Direct Process for producing alkylhalosilanes is well-known and has been refined and modified in many ways since Rochow first described preparing alkylhalosilanes by contacting alkylhalides with silicon at elevated temperatures. This process is used for producing virtually all commercial alkylhalosilanes in the world today.

Rochow, U.S. Pat. No. 2,380,995, teaches passing a gaseous stream of methyl chloride into a heated tube where it contacted powdered silicon at about 300° C. Rochow obtained a mixture comprising 52 weight percent methyltrichlorosilane, 14.5 weight percent dimethyldichlorosilane, and lessor amounts of other silanes. The reaction between silicon and the gaseous hydrocarbon halide is facilitated by the presence of a metallic catalyst such as copper. Furthermore, Rochow teaches that the copper may be alloyed with the silicon.

Rochow et al., U.S. Pat. No. 2,380,996, teach an improved method where a solid porous contact mass formed of powdered silicon and powdered copper is reacted with a hydrocarbon halide. This method continues to be a method of choice for the commercial production of dialkyldihalosilanes, since use of the powdered materials provide for better control of the process than when a silicon-copper alloy is used.

The requirements on the silicon in terms of chemical composition and particle size distribution for the direct synthesis of methylchlorosilanes from silicon and methyl chloride have been investigated thoroughly. Chemical grade silicon metal employed in the direct synthesis of methylchlorosilanes typically has an elemental composition of 0.100 to 0.280 Wt. % aluminum, 0 to 0.150 Wt. % calcium, 0.150 to 0.500 Wt. % iron and 0.015 to 0.050 Wt. % titanium. Chemical composition can enhance the reactivity and selectivity of the reaction to produce the alkylhalosilanes. However, small amounts of particular elements are known to adversely affect reactivity and selectivity. The silicon particle size and distribution plays a key role in reactivity and selectivity of the reaction as well. Freeburne et al., U.S. Pat. No. 5,312,948, teaches an improved process for the reaction of an alkyl halide with particulate silicon in a fluidized-bed. The improvement comprises controlling the particle size of the silicon to within a range of one micron to 85 microns.

The silicon structural composition and its influence on the reaction with methyl chloride have been the subject of numerous scientific studies. It was determined that the silicon structure can be influenced by the cooling process used during production of the silicon. For example, cooling the silicon by a process such as atomization was found to increase production rates of the direct synthesis of methylchlorosilanes from silicon and methyl chloride. Feldner et al., U.S. Pat. No. 5,015,751 teach a process for the production of organochlorosilanes using silicon produced by atomizing with an inert gas or a suitable alloy of silicon produced by atomizing with an inert gas. The atomized silicon chemical composition was 0.05–1% by weight Fe; 0.01–1% by weight Al; 0.0001–1% by weight Ca; 0–0.5% by weight Na; 0–0.5% by weight Li; 0–0.5% by weight K; 0–0.5% by weight Mg; 0–0.5% by weight Sr; 0–0.5% by weight Ba; 0–0.5% by weight Be; and the remainder other impurities in small amounts.

Pachaly et al., U.S. Pat. No. 5,334,738, teach the preparation of methylchlorosilanes from silicon and methylchloride in the presence of a copper catalyst and optional promoter substances. The structural parameter QF of the silicon employed in the method is determined by (a) cutting up silicon test specimens to form a cut surface, (b) totaling on the cut surface the areas of precipitates of intermetallic phases having a longitudinal shape to give an area number A, (c) totaling on the cut surface the areas of precipitates of intermetallic phases having a circular shape to give an area number B, and (d) obtaining the quotient of the area number A and the area number B, called the structural parameter QF. Pachaly et al. disclosed employing water granulated silicon in the method.

Margaria, U.S. Pat. No. 5,605,583, teaches using metallurgical silicon containing, by weight, 0.25% iron with controlled microstructure for the preparation of halogenosilanes. The microstructure is characterized by an image obtained with a scanning electron microscope. Degen et al., U.S. Pat. No. 5,380,903, teach metallic silicon for the Rochow-Synthesis is reduced to particles measuring at least 5 mm in their smallest dimension and 15 mm in their largest dimension, cooling the silicon from a temperature of at least 700° C. to at most 120° C. within a maximum of 2 seconds, and then ground and reacted.

The present invention provides a process for using less expensive particulate water granulated silicon containing higher levels of iron and titanium in the Direct Process for the preparation of alkylhalosilanes. The inventors have unexpectedly discovered that less expensive particulate water granulated silicon performance in the Direct Process is comparable to that of the higher cost conventionally cast silicon containing lower levels of iron.

SUMMARY OF INVENTION

The present invention is a process for the use of water granulated silicon in the preparation of alkylhalosilanes. The process comprises contacting an alkyl halide described by formula RX, with a particulate water granulated silicon containing greater than 0.5 to about 5.0 weight percent iron, in the presence of a catalyst composition comprising copper, at a temperature within a range of about 250° C. to 350° C., where R is selected from the group consisting of alkyls comprising one to about four carbon atoms and X is a halogen. The present invention provides a process for using less expensive particulate water granulated silicon containing higher levels of iron and titanium in the Direct Process for the preparation of alkylhalosilanes.

DESCRIPTION OF INVENTION

The present invention is a process for the use of water granulated silicon in the preparation of alkylhalosilanes. The process comprises contacting an alkyl halide described by formula RX, with a powdered water granulated silicon containing greater than 0.5 to about 5.0 weight percent iron, in the presence of a catalyst composition comprising copper, at a temperature within a range of about 250° C. to 350° C., where R is selected from the group consisting of alkyls comprising one to about four carbon atoms and X is a halogen.

The alkylhalosilanes which can be prepared by the present process are those described by formula $R_aH_bSiX_{4-a-b}$, where each R is independently selected from a group consisting of alkyls comprising one to four carbon atoms, a=0, 1, 2, 3, or 4, b=0, 1, 2, or 3, a+b=1, 2, 3 or 4, and X is a halogen. The substituent R can be, for example, methyl, ethyl, propyl, isopropyl, butyl, and tert-butyl. The preferred alkylhalosilanes are those having the formula $R_2SiX_2$, where R is methyl or ethyl and X is chlorine. The most preferred alkylhalosilane is dimethyldichlorosilane, i.e. $(CH_3)_2SiCl_2$.

In the present process an alkyl halide is contacted with the particulate water granulated silicon containing greater than 0.5 to about 5.0 weight percent iron. Alkyl halides useful in the present process are described by formula RX, where R and X are as previously described. The preferred alkyl halide is methyl chloride.

Contact of the alkyl halide with the particulate water granulated silicon containing greater than 0.5 to about 5.0 weight percent iron can be effected in standard reactors for effecting such contact such as a vibrating bed or fluidized-bed reactor. In a preferred process the contact is effected in a standard fluidized-bed reactor. The bed can be fluidized using the alkyl halide as the fluidizing media or using a mixture of the alkyl halide with an inert gas in the process as the fluidizing media.

The particulate water granulated silicon used in the present process is prepared by pouring molten silicon into water to control the cooling rate of the silicon during solidification. By rapidly cooling the liquid silicon, a gain size of about 50 to 100 microns may be obtained. The particulate water granulated silicon can have 0.5 to about 5.0 percent by weight iron, 0 to 1 percent by weight aluminum, 0 to 8 percent by weight calcium and 0.05 to 0.30 percent by weight titanium and greater than 90 percent silicon. Preferably the particulate water granulated silicon contains 1.0 to about 4.0 percent by weight iron and 0.05 to 0.20 percent by weight titanium. Most preferably the particulate water granulated silicon contains 1.5 to about 3.5 percent by weight iron and about 0.07 to 0.15 percent by weight titanium.

In the present process, it is desirable that the particulate water granulated silicon have a particle ground size within a range of one micron to about 150 micron. Preferred, the particulate water granulated silicon particle size is within a range of one micron to about 85 micron. Most preferred, the silicon particle size is within a range of about two to 50 microns. It is preferred that the particulate water granulated silicon have a particle size mass distribution characterized by a 10th percentile of 2.1 to 6 microns, a 50th percentile of 10 to 25 microns, and a 90th percentile of 30 to 60 microns. Most preferred is when the particle size mass distribution of the particulate water granulated silicon is characterized by a 10th percentile of 2.5 to 4.5 microns, a 50th percentile of 12 to 25 microns, and a 90th percentile of 35 to 45 microns.

The method of making the particle size distributions useful in the present process is not critical. Standard methods for sizing particulate silicon can be used, for example, a roller or ball mill may be used to grind the water granulated silicon particulate to alter the size distribution. The particulate water granulated silicon may be further classified as to particle size distribution by means of, for example, screening or use of mechanical classifiers such as a rotating classifier.

The present process is conducted in the presence of a catalyst composition comprising copper. The present process requires the presence of copper as a catalyst within a range of about 0.1 to 10 weight percent of the silicon present in the process. The source of the copper added to the process may be powdered copper metal, powdered silicon-copper alloy, a compound of copper, or a mixture of two or more sources of copper. The copper compound may be, for example, cuprous chloride.

In addition to copper, the catalyst composition may employ other metals as catalysts. The scope of other metals contemplated as catalysts are those metals known to those skilled in the art as promoters of the Direct Process. Examples of such catalytic metals are described by and incorporated by reference herein, Halm et al., U.S. Pat. No. 4,602,101; Halm et al., U.S. Pat. No. 4,946,978; Halm et al., U.S. Pat. No. 4,762,940; and Ward et al., U.S. Pat. No. Re. 33,452. These catalytic metals include, for example, phosphorous, phosphorous compounds, zinc, zinc compounds, tin, tin compounds, and mixtures thereof.

A preferred catalyst composition for the present process comprises on an elemental basis by weight: 0.1 to 10 weight percent copper based on silicon present in the process, 50 to 10,000 ppm zinc, 5 to 200 ppm tin, and 25 to 2,500 ppm phosphorous.

The process can be conducted at a temperature within a range of about 250° C. to 350° C. The preferred temperature for conducting the present process is within a range of about 260° C. to 320° C. Even more preferred is a temperature within a range of about 280° C. to 320° C.

The following examples are offered to illustrate the present invention. These examples are not intended to limit the scope of the present claims.

EXAMPLE 1

Evaluation of chemical grade conventionally cast silicon in the Direct Process. A mixture comprising chemical grade conventionally cast silicon (aluminum=0.129 Wt. %, iron=0.302 Wt. %, calcium=0.007 Wt. %, and titanium=0.029 Wt. %), 6.5 Wt. % cuprous chloride, 600 ppm brass (50 Wt. % zinc), 46 ppm tin, and 2000 ppm copper phosphorus alloy, was formed. The particle size mass distribution of the silicon was characterized as a 10th percentile of 1.8$\mu$, a 50th percentile of 15$\mu$, and a 90th percentile of 49$\mu$.

The mixture was charged to a reactor similar to that described by Mass et al., U.S. Pat. No. 4,218,387. The reactor temperature was maintained at about 315° C. by means of a constant temperature bath. The reactor was purged for 15 minutes with nitrogen gas. The nitrogen purge was then shut off and methyl chloride gas was fed to the reactor for a total of 44 hours during which time all products and unreacted methyl chloride were collected in a cold trap. Weight loss of the reactor was used as an indicator of silicon conversion. The liquid collected in the cold trap was analyzed by gas chromatography (GC) using a thermal conductivity (TC) detector. The performance of the silicon was calculated as the weight fraction of silicon consumed times the weight percent of dimethyldichlorosilane as a percent of the total weight of silane products formed. The average silicon performance was determined to be 77.3 percent.

EXAMPLE 2

Evaluation of high impurity conventionally cast silicon in the Direct Process. A mixture comprising high impurity conventionally cast silicon (aluminum=0.189 Wt. %, iron=

1.590 Wt. %, calcium=0.037 Wt. %, titanium=0.105 Wt. %), 6.5 Wt. % cuprous chloride, 600 ppm brass (50 Wt. % zinc), 46 ppm tin, and 2000 ppm copper phosphorus alloy, was formed. The particle size mass distribution of the silicon was characterized as a 10th percentile of 1.9$\mu$, a 50th percentile of 15$\mu$, and a 90th percentile of 57$\mu$. The mixture was analyzed and silicon performance calculated as described in Example 1. The average silicon performance was determined to be 67.

EXAMPLE 3

Evaluation of high impurity conventionally cast silicon in the Direct Process. A mixture comprising high impurity conventionally cast silicon (aluminum=0.189 Wt. %, iron=1.670 Wt. %, calcium 0.037 Wt. %, titanium=0.106 Wt. %), 6.5 Wt. % cuprous chloride, 600 ppm brass (50 Wt. % zinc), 46 ppm tin, and 2000 ppm copper phosphorus alloy, was formed. The particle size mass distribution of the silicon was characterized as a 10th percentile of 1.9$\mu$, a 50th percentile of 15$\mu$, and a 90th percentile of 57$\mu$. The mixture was analyzed and silicon performance calculated as described in Example 1. The average silicon performance was determined to be 67.8.

EXAMPLE 4

Evaluation of chemical grade conventionally cast silicon in the Direct Process. A mixture comprising chemical grade conventionally cast silicon (aluminum=0.178 Wt. %, iron=0.448 Wt. %, calcium=0.004 Wt. %, titanium=0.044 Wt. %), 6.5 Wt. % cuprous chloride, 600 ppm brass (50 Wt. % zinc), 46 ppm tin, and 2000 ppm copper phosphorus alloy, was formed. The particle size mass distribution of the silicon was characterized as a 10th percentile of 2.0$\mu$, a 50th percentile of 16$\mu$, and a 90th percentile of 62$\mu$. The mixture was analyzed and silicon performance calculated as described in Example 1. The average silicon performance was determined to be 85.6.

EXAMPLE 5

Evaluation of high impurity particulate water granulated silicon in the Direct Process. A mixture comprising high impurity particulate water granulated silicon (aluminum=0.172 Wt. %, iron=1.72 Wt. %, calcium=0.006 Wt. %, titanium=0.087 Wt. %), 6.5 Wt. % cuprous chloride, 600 ppm brass (50 Wt. % zinc), 46 ppm tin, and 2000 ppm copper phosphorus alloy, was formed. The particle size mass distribution of the silicon was characterized as a 10th percentile of 1.9$\mu$, a 50th percentile of 15$\mu$, and a 90th percentile of 58$\mu$. The mixture was analyzed and silicon performance calculated as described in Example 1. The average silicon performance was determined to be 88.9.

EXAMPLE 6

Evaluation of high impurity particulate water granulated silicon in the Direct Process. A mixture comprising high impurity particulate water granulated silicon (aluminum=0.147 Wt. %, iron=1.78 Wt. %, calcium=0.004 Wt. %, titanium=0.090 Wt. %), 6.5 Wt. % cuprous chloride, 600 ppm brass (50 Wt. % zinc), 46 ppm tin, and 2000 ppm copper phosphorus alloy, was formed. The particle size mass distribution of the silicon was characterized as a 10th percentile 1.9$\mu$, a 50th percentile of 16$\mu$, and a 90th percentile of 60$\mu$. The mixture was analyzed and silicon performance calculated as described in Example 1. The average silicon performance was determined to be 89.5.

We claim:

1. A process for the preparation of alkylhalosilanes comprising contacting an alkyl halide described by formula RX, with a particulate water granulated silicon containing greater than 0.5 to about 5.0 weight percent iron in the presence of a catalyst composition comprising copper, at a temperature within a range of about 250° C. to 350° C., where R is selected from a group consisting of alkyls comprising one to about four carbon atoms and X is a halogen.

2. A process according to claim 1, where the particulate water granulated silicon contains 1.0 to about 4.0 weight percent iron.

3. A process according to claim 1, where the water particulate granulated silicon contains 1.5 to about 3.5 weight percent iron.

4. A process according to claim 1, where the particulate water granulated silicon contains about 0.05 to 0.30 weight percent titanium.

5. A process according to claim 1, where the particulate water granulated silicon contains about 0.05 to 0.2 weight percent titanium.

6. A process according to claim 1, where the alkyl halide is methylchloride.

7. A process according to claim 1, where the alkylhalosilane is dimethyldichlorosilane.

8. A process according to claim 1, where the temperature is within a range of about 270° C. to 320° C.

9. A process according to claim 1, where X is chlorine.

10. A process for the preparation of alkylhalosilanes comprising contacting an alkyl halide described by formula RX, with a particulate water granulated silicon containing greater than 0.5 to about 5.0 weight percent iron, and greater than about 0.05 to 0.30 weight percent titanium, in the presence of a catalyst composition comprising copper, at a temperature within a range of about 250° C. to 350° C., where R is selected from a group consisting of alkyls comprising one to about four carbon atoms and X is a halogen.

11. A process according to claim 10, where the alkyl halide is methylchloride.

12. A process for the preparation of alkylhalosilanes comprising contacting an alkyl halide described by formula RX, with a particulate water granulated silicon containing greater than 0.05 to about 0.30 weight percent titanium in the presence of a catalyst composition comprising copper, at a temperature within a range of about 250° C. to 350° C., where R is selected from a group consisting of alkyls comprising one to about four carbon atoms and X is a halogen.

13. A process according to claim 12, where the particulate water granulated silicon contains 0.5 to about 5.0 weight percent iron.

* * * * *